United States Patent
Min et al.

(10) Patent No.: US 11,801,331 B2
(45) Date of Patent: Oct. 31, 2023

(54) COMPOSITION FOR CARTILAGE REGENERATION AND PREPARING THEREOF

(71) Applicant: ATEMS CO., LTD., Suwon-si (KR)

(72) Inventors: Byoung-Hyun Min, Anyang-si (KR); So Ra Park, Incheon (KR); Byung Hyune Choi, Incheon (KR); Young Jick Kim, Gimhae-si (KR); Hyun Ju Oh, Seoul (KR)

(73) Assignee: ATEMS CO., LTD., Suwon-si (KR)

( * ) Notice: Subject to any disclaimer, the term of this patent is extended or adjusted under 35 U.S.C. 154(b) by 209 days.

(21) Appl. No.: 16/322,193

(22) PCT Filed: Aug. 2, 2017

(86) PCT No.: PCT/KR2017/008353
§ 371 (c)(1),
(2) Date: Jan. 31, 2019

(87) PCT Pub. No.: WO2018/026198
PCT Pub. Date: Feb. 8, 2018

(65) Prior Publication Data
US 2019/0184061 A1 Jun. 20, 2019

(30) Foreign Application Priority Data

Aug. 2, 2016 (KR) .................. 10-2016-0098658

(51) Int. Cl.
*A61L 27/38* (2006.01)
*A61K 35/32* (2015.01)
*A61K 35/12* (2015.01)
*A61L 27/36* (2006.01)
*C12N 5/077* (2010.01)

(52) U.S. Cl.
CPC .......... *A61L 27/3817* (2013.01); *A61K 35/12* (2013.01); *A61K 35/32* (2013.01); *A61L 27/3633* (2013.01); *A61L 27/3654* (2013.01); *A61L 27/3691* (2013.01); *A61L 27/3852* (2013.01); *A61L 27/3895* (2013.01); *C12N 5/0655* (2013.01); *A61L 2430/06* (2013.01); *C12N 2500/12* (2013.01); *C12N 2500/38* (2013.01); *C12N 2501/15* (2013.01); *C12N 2501/33* (2013.01); *C12N 2501/39* (2013.01); *C12N 2501/998* (2013.01)

(58) Field of Classification Search
None
See application file for complete search history.

(56) References Cited

PUBLICATIONS

Jin RL, Park SR, Choi BH, Min BH. Scaffold-free cartilage fabrication system using passaged porcine chondrocytes and basic fibroblast growth factor. Tissue Eng Part A. Aug. 2009;15(8):1887-95. (Year: 2009).*
Park K, Huang J, Azar F, Jin RL, Min BH, Han DK, Hasty K. Scaffold-free, engineered porcine cartilage construct for cartilage defect repair—in vitro and in vivo study. Artif Organs. Aug. 2006;30(8):586-96. (Year: 2006).*
Choi WH, Kim HR, Lee SJ, et al. Fetal Cartilage-Derived Cells Have Stem Cell Properties and Are a Highly Potent Cell Source for Cartilage Regeneration. Cell Transplantation. 2016;25(3):449-461. (Online prepub date Jul. 13, 2015) (Year: 2015).*
Sophia Fox AJ, Bedi A, Rodeo SA. The basic science of articular cartilage: structure, composition, and function. Sports Health. 2009;1(6):461-468. (Year: 2009).*
Huang BJ, Hu JC, Athanasiou KA. Effects of passage number and post-expansion aggregate culture on tissue engineered, self-assembled neocartilage. Acta Biomater. 2016;43:150-159. (Year: 2016).*
Park et al. "Engineered cartilage utilizing fetal cartilage-derived progenitor cells for cartilage repair" (2020), Nature: Scientific Reports, 10:5722 , 1-12 (Year: 2020).*
Anvar Khodiev; "Chondrocyte implantation for treatment of articular cartilage"; International Journal of Clinical Rheumatology; 2021; 16(8), 239-248.
Nele Pascale Grigull et al; "Chondrogenic Potential of Pellet Culture Compared to High-Density Culture on a Bacterial Cellulose Hydrogel"; International Journal of Molecular Sciences; 2020, 21, 2785; pp. 1-16.
MACI Product Brochure; Vericel Corporation, 2020 (6 pages total).

* cited by examiner

Primary Examiner — Teresa E Knight
(74) Attorney, Agent, or Firm — Sughrue Mion, PLLC

(57) ABSTRACT

The present invention provides a cartilage regenerating composition including a fetal cartilage tissue-derived cell and an extracellular matrix derived from a fetal cartilage tissue, and a preparing method thereof. According to the present invention, the cartilage-regenerating composition may produce a three-dimensional tissue of a size suitable for use as a cartilage without a scaffold, may be easily transplantable regardless of the size and shape of the cartilage defect at the site of administration since it can be administered in the form of a gel, but has high application and adhesion, may exhibit a high binding ability to the host tissue, and may have a phenotype of mature cartilage tissue, thereby exhibiting an excellent cartilage regeneration effect.

7 Claims, 9 Drawing Sheets

Human infant chondrocyte artificial cartilage tissue

Human fetal chondrocyte artificial cartilage tissue

COMPOSITION FOR CARTILAGE REGENERATION AND PREPARING THEREOF

TECHNICAL FIELD

The present invention relates to a cartilage-regenerating composition and a preparing thereof.

BACKGROUND ART

Cartilage is a tissue composed of only extracellular matrix and cartilage cells as single cells. A cartilage tissue has neither no blood vessels nor nerve, so it is difficult to heal the cartilage tissue when it is damaged. In addition, a cartilage cell is surrounded by hard extracellular matrix, and thus they are difficult to regenerate once damaged or degenerated.

Drug treatments (such as analgesics, steroids, or non-steroidal anti-inflammatory drugs) cartilage protectants (such as hyaluronic acid, glucosamine, or chondroitin), or surgical procedures (such as arthroscopic surgery, proximal tibial osteotomy, total knee arthroplasty, or bone-cartilage tissue grafting) may be used to treat damaged cartilage tissue. However, the drug treatment only has an effect of relieving the pain or the inflammatory reaction itself non-specifically, and the cartilage protectants temporarily protect the joints by merely nourishing the cartilage cells or alleviating the shocks. In addition, various orthopedic surgical procedures are performed, and representative methods therefor include bone marrow stimulation and osteochondral graft. The bone marrow stimulation is a relatively simple operation using a method of filling a cartilage with a blood clot containing stem cells derived from marrow by exposing damaged subchondral bone, but it is disadvantageous in that it is regenerated as fibrocartilage rather than hyaline cartilage after surgery. The osteochondral graft is a treating method of collecting osteo-cartilage connective tissue at a site that receives less weight in the patient's own cartilage tissue and then transplanting it to the cartilage damage site, but it is disadvantageous in that it cannot be used for a large damage site.

Many cell therapy agents supplying therapeutic cells from outside have been studied in order to overcome the disadvantages of such surgical treatment techniques. The first commercialized technique is autologous chondrocytes implantation (ACI), which removes a small amount of healthy cartilage from the area of the patient's own cartilage tissue which is underweight and separates the cartilage cells therefrom to perform in-vitro incubation thereof, and then injecting it into the damage site, but it is disadvantageous in that the two surgeries are cumbersome and the healthy cartilage is damaged. First of all, the number of chondrocytes that is collected should be incubated for a certain period of time, and the demineralization phenomenon that loses the chondrocyte characteristics during the cultivation period occurs, and the chondrocytes injected are heterogeneous and concentrated on specific sites due to gravity, which are irregularly distributed.

Stem cell transplantation studies have been actively conducted to overcome such issues, and a technique has been recently commercialized for incubating the same type of umbilical cord blood-derived mesenchymal stem cells and transplanting it into a damaged cartilage site. Techniques for treating cartilage damage by separately incubating mesenchymal stem cells in bone marrow or adipose tissue have been actively studied in addition to umbilical cord blood, but these are not expected to be a universal treatment method since the basis for the survival of injected mesenchymal stem cells is poor and the differentiation into chondrocytes and the efficiency of cartilage formation in vivo after transplantation are not proved. In conclusion, cell therapy agents for injecting chondrocytes or stem cells into cartilage damage site has poor evidence for cell survival, differentiation, and distribution, and its mechanism of action has not been elucidated, and the relative efficacy of the cell therapy agents has not been studied, whereby it is unlikely to be recognized as a clinically recommended treatment.

There have been used techniques of delivering cells using various types of biomaterials as scaffolds in order to overcome the disadvantages of in vivo distribution and differentiation of cell therapeutic agents due to the above problems, and furthermore, techniques for producing a three-dimensional tissue engineered cartilage in vitro have been developed.

The scaffolds currently used for cell delivery at the transplantation site have various forms such as sponges, gels, fibers and microbeads, and are mainly produced using natural or synthetic biomaterials. In case of using the scaffolds, the transplantation itself has a high efficiency and may distribute evenly in the graft site, but when the cells proliferate in the scaffolds or the extracellular matrix is secreted, the scaffolds may cause spatial limitation. In particular, hydrogel-type scaffolds have a disadvantage in that oxygen and nutrients are not smoothly supplied and the cell survival rate and cartilage differentiation decrease, and the membrane-type scaffolds may not form three-dimensional cartilage tissue. When three-dimensional sponge or mesh-type scaffolds are used, a prepared artificial cartilage has a low binding force with a host tissue, and cartilage regeneration is not good. In addition, all the scaffolds are decomposed, and in the case of a natural biological material with a rapid decomposition speed, it is likely to cause cell loss during the decomposition. As a result, the cell therapy agents using the scaffolds are not proved to be relatively effective with conventional cell therapy agents, so it is not a situation where priority selection is recommended.

Separately from the above techniques, studies have been conducted to produce an artificial cartilage material having a chemical composition similar to cartilage by inoculating cells with a bio-material and then incubating the cells in a bioreactor together with bioactive factors, and a technique for making artificial cartilage tissue without using the scaffolds have also been developed. For example, a method of making artificial cartilage by applying a bioreactor after inoculating a cell into an incubating dish at a high concentration, a method of increasing the cell proliferation and differentiation by adding a fetal serum and growth factor to the incubating medium, and a method of producing various cells in the form of pellets by centrifugation have been reported. However, most of these techniques have been made of thin membrane type with a thickness of several tens of micrometers (mm) or small pellet type with a diameter of about 1 mm, which is small in size for practical use as a cartilage and exhibits a sufficient regeneration effect.

Research and development of a cartilage regeneration material capable of replacing cartilage tissue under the above problems has been continuously carried out, and in particular, they are aimed to solve the following contents for use as a cartilage regeneration material suitable for a human body.

First, the size and volume should be large enough to fix the transplanted cartilage.

Second, since articular cartilage defects are usually atypical, artificial cartilage should be able to adapt to such atypical defect types.

Third, since the in vitro incubated cartilage cannot be similar to the natural cartilage histologically, it needs to be able to differentiate and remodel by the environment in the body after transplant rather than complete the tissue in vitro, and the integration with surrounding tissues should be well performed in the remodeling process.

However, when large cartilage is made, the present technique causes necrosis of central tissue, and is difficult to solve because of the difficulty in manufacturing cartilage complex. In addition, for example, artificial cartilage tissue produced using three-dimensional scaffolds has a disadvantage in that when the cartilage is transplanted into a damaged cartilage tissue, its integration with surrounding tissues is not good because the physical property of the artificial cartilage tissue changes rigidly in vitro. In addition, in vitro incubated cartilage may cause rejection in the human body or does not have sufficient stability in terms of fusion reaction with tissues.

Accordingly, the present inventors have completed the present invention by carrying out research and development on a composition for regenerating cartilage suitable for the human body while solving the above-mentioned three problems.

PRIOR ART DOCUMENT

Patent Document (Patent Document 0001) KR10-1340458, 2013.12.11.
(Patent Document 0002) KR10-0917422, 2009.09.22.

DISCLOSURE

Technical Problem

An object of the present invention is to provide a cartilage regenerating composition including a fetal cartilage tissue-derived cell and an extracellular matrix derived from a fetal cartilage tissue.

Technical Solution

An object of the present invention is to provide a method for producing the cartilage regenerating composition.

An object of the present invention is to provide a pharmaceutical composition for treating a cartilage defect disease including the cartilage regenerating composition as an active ingredient.

An object of the present invention is to provide a method for treating a cartilage defect disease by administering to a patient a pharmaceutically effective amount of the cartilage regenerating composition.

An object of the present invention is to provide a use of the cartilage regenerating composition in the preparing of a medicament for the treatment of cartilage defect diseases.

In the present invention, the term "fetal cartilage tissue-derived cell" refers to a cell isolated from a fetal cartilage tissue, and may be chondrocytes isolated after complete digestion of cartilage tissue using collagenase and the like.

In the present invention, the term "extracellular matrix derived from the fetal cartilage tissue" is a collection of biopolymers synthesized by cells from fetal cartilage tissue-derived cells and composed of molecules secreted and accumulated extracellularly, including fibrous proteins such as collagen and elastin, complex proteins such as glycosaminoglycan, cell adhesion proteins such as fibronectin and laminin.

In the present invention, the term "cartilage" includes hyaline cartilage, fibrocartilage, or elastic cartilage, and is not particularly limited. The cartilage includes articular cartilage, ear cartilage, nasal cartilage, elbow cartilage, meniscus, knee cartilage, costal bone, ankle cartilage, tracheal cartilage, larynx cartilage and vertebral cartilage without any limitation to regions of cartilage.

In the present invention, the term "regeneration" generally refers to an action that, when an organism has lost some of its body or its function, it re-forms the tissue or organ of that part to restore it to its original state or restore its function. This regeneration ability is stronger as the system is simple and systematic and the degree of evolution is low.

In the present invention, the term "cartilage-regenerating composition" is a composition exhibiting cartilage regeneration ability when implanted in a cartilage defect or a damaged part, thereby exhibiting improvement and therapeutic effect on cartilage damage.

In the present invention, the term "gel" refers to a jelly-like material, indicating a solid that has a soft, weak to strong and rough range of properties and does not show flow in a steady state, and most of the weight of gels generally behaves like solids due to liquid or three-dimensional network structure.

In the present invention, the term "cartilage defect disease" refers to a disease caused by cartilage defects, injuries, or defects caused by cartilage, cartilage tissue and/or joint tissues (synovial membrane, articular capsule, cartilaginous bone, etc.) injured by mechanical stimulation or inflammatory reaction. Such cartilage defect diseases include, but are not limited to, degenerative arthritis, rheumatoid arthritis, fractures, muscle tissue damage, plantar fasciitis, humerus ulcer, calcified myositis, or joint damage caused by fracture nonunion or trauma.

In the present invention, the term "physical strength" refers to the degree of physical strength to withstand a stimulus, and preferably refers to a compressive strength, which is a value obtained by dividing a compressive load at a cross-section under compression caused by a vertical stress by a cross-sectional area of the sample. In the present invention, the compressive strength indicates a value obtained by measuring the Young's modulus at a strain of 10 to 16% when the sample is pressed at a rate of 1 min/min.

In the present invention, the term "coating property (spreadability)" refers to the property of spreading during physical properties, and when applied to the affected part, it does not become a lump and spreads smoothly over the surface. In the present invention, the spreadability refers to the degree of spreading of a sample per unit weight when a force of 5 N is vertically applied to the sample for 1 second at a rate of 1 mm/min.

In the present invention, the term "adherence" refers to a property that a substance adheres to a substance, and refers to a property that the substance does not fall off when adhered to the affected part. In the present invention, the adherence refers to the resistance until a substance is in contact with the affected part and the jig having a diameter of 5 mm and attached thereto and then is separated therefrom by pulling it at a speed of 1.3 mm/min.

In the present invention, the term "cartilage differentiation medium" refers to a medium capable of facilitating the in vitro growth and survival of the cartilage-generating composition and supplying nutrients for being made into the cartilage-regenerating composition, and the medium includes both the substrate etc. secreted from the cells during the incubation period and the nutrients etc., remaining in the cell incubation.

In the present invention, the term "transplantation" generally refers to the process of transferring the donor's cells, tissues or organs of the donor to damaged tissue or organ of to the recipient, and indicating that the application of cartilage-regenerating compositions to cartilage defects, damage, and defect sites. The transplantation may be carried out by methods known in the art. For example, a surgical operation may be performed, and may be injected directly into the affected part.

In the present invention, the term "pharmacologically effective amount" refers to an amount sufficient to treat a disease at a reasonable benefit/risk ratio applicable to medical treatment, and an effective dose level may be determined by the species and severity, age, sex, type of disease, duration of treatment, factors including co-administered drugs, and factors well known in other medical disciplines.

In the present invention, the term "patient" refers to all animals including humans with cartilage defect disease, and indicates a group capable of improving cartilage regeneration and treating the cartilage by administering the cartilage-regenerating composition.

The present invention provides a cartilage regenerating composition including a fetal cartilage tissue-derived cell and an extracellular matrix derived from a fetal cartilage tissue.

According to the present invention, the cartilage-regenerating composition may produce a three-dimensional tissue of a size suitable for use as a cartilage without a scaffold, may be easily transplantable regardless of the size and shape of the cartilage defect at the site of administration since it can be administered in the form of a gel, but has high application and adhesion, may exhibit a high binding ability to the host tissue, and may have a phenotype of mature cartilage tissue, thereby exhibiting an excellent cartilage regeneration effect. In particular, the cartilage-regenerating composition has a strength lower than that of a real cartilage matured outside the human body, but has a merit of being easy to apply to the affected part since it has a gel form, and has similar strength to that of the actual cartilage through maturation and reforming at the transplantation site in vivo.

A cartilage-regenerating composition including a fetal cartilage tissue-derived cell and a fetal cartilage tissue-derived extracellular matrix may be prepared by the following steps:
  (a) separating and incubating chondrocytes in fetal cartilage tissue;
  (b) obtaining a cell membrane including the incubated chondrocytes and an extracellular matrix thereof;
  (c) centrifuging the obtained cell membrane to obtain a cell pellet; and
  (d) incubating the cell pellet in cartilage differentiation medium.

The cartilage regeneration composition including the fetal cartilage tissue-derived cells and the fetal cartilage tissue-derived extracellular matrix produced by the above steps has the following properties:
  Shape: gel type
  Compressive strength: Young's modulus applied when the strain of the tissue changes between 10 and 16% at a rate of 1 mm/min in the in vitro state after manufacture is 20 kPa or less, is preferably in a range of 0.2 to 20 kPa, more preferably 4.1 to 20 kPa to 18.9 kPa;
  Applicability: the area of spread per unit weight (1 mg) of a force of 5 N applied at 1 mm/min for 1 second in vitro after preparation is 0.1 to 2.0 $mm_2$/mg, 1.7 mm/mg, more preferably 0.4 to 1.2 mm/mg;
  Adherence: after the preparation, the substance is contacted with a jig and a ring of 5 mm in diameter in the in vitro state, and then pulled at a rate of 1.3 mm/min, adhesion of 0.5 to 5.0 kPa, is preferably 0.9 to 4.5 kPa, more preferably 1.0 to 2.8 kPa.

According to the present invention, the cartilage-regenerating composition may be transplanted into the affected part by applying a gel form, and may be applied and spread. According to the present invention, the cartilage-regenerating composition has excellent coating property as described above before, in vitro, or immediately after preparation in vivo, so that the cartilage-regenerating composition can be well spread during application of the affected part. According to the present invention, the cartilage-regenerating composition has excellent adhesion as described above before, in vitro, or immediately after preparation in vivo, so that the cartilage-regenerating composition can be regenerated into cartilage tissue without falling off the affected part when applied to the affected part.

In the present invention, the cartilage-regenerating composition may maintain the gel form at 25 to 37° C. for at least 24 hours, more preferably at least 24 hours but less than one year. The cartilage-regenerating composition may be 1 mm to 15 mm in diameter and 1 to 15 mm in height in the step of incubating the cell pellet in the cartilage differentiation medium. In addition, in the step of incubating the cell pellet in the cartilage differentiation medium, it is possible to maintain the optimum condition for cartilage regeneration by controlling the compressive strength, coating property and adherence according to the incubating period.

The cartilage-regenerating composition exhibits the characteristic of the mature cartilage as the expression of glycoprotein and second collagen are increased over time after application into vivo condition, preferably human body.

The present invention provides a preparing method of a cartilage-regenerating composition including a fetal cartilage tissue-derived cell and an extracellular matrix derived from a fetal cartilage tissue.

According to the present invention, the preparing method of the cartilage-generating composition may provide gel-like physical properties depending on cell pellet formation and incubating therefrom and may provide the cartilage-regenerating composition suitable for the human body by controlling physical properties of the composition for regenerating cartilage produced by controlling the incubation period.

The preparing method of the cartilage-regenerating composition including a fetal cartilage tissue-derived cell and a fetal cartilage tissue-derived extracellular matrix may include the following steps:
  (a) separating and incubating chondrocytes in fetal cartilage tissue;
  (b) obtaining a cell membrane including the incubated chondrocytes and an extracellular matrix thereof;
  (c) centrifuging the obtained cell membrane to obtain a cell pellet; and
  (d) incubating the cell pellet in cartilage differentiation medium.

The cartilage-regenerating composition includes (a) separating and incubating chondrocytes in fetal cartilage tissue.

The fetal cartilage tissue may be separated from the joint region (e.g., a knee joint) of the fetus. The isolated fetal cartilage tissue may be obtained by collecting the cells that have been treated with a protease such as collagenase, pepsin and the like, after the cartilage tissue has been degraded. The isolated chondrocyte precursor cells may be grown to produce extracellular matrix while being incubated under incubation medium (for example, medium supplemented with FBS and antibiotic under DMEM).

The preparing method of the cartilage-regenerating composition includes (b) obtaining a cell membrane including the incubated chondrocytes and an extracellular matrix thereof.

Unlike a general method for obtaining cells, the preparing method according to the present invention is to obtain the cell membrane including the incubated chondrocytes and its extracellular matrix. That is, when the cells are separated from the incubation dish, they are obtained including all of the chondrocytes and its extracellular matrix in the incubation dish without separating the cells into single cells. This can be accomplished by removing the incubation medium, treating trypsin-EDTA, etc. and collecting the entire membrane containing the extracellular matrix with the cells attached to the bottom.

The preparing method of the cartilage-regenerating composition includes (c) centrifuging the obtained cell membrane to obtain a cell pellet.

The cell membrane obtained in the step (b) may form an aggregate (i.e., pellet form) through centrifugation. The formation of such a pellet form may be preferably prepared by centrifugation at 100 g to 500 g for 5 minutes to 30 minutes, more preferably, under a cartilage differentiation medium containing cartilage differentiation factors.

The cartilage differentiation medium is preferably selected from at least one of the group consisting of insulin, human transferrin, sodium selenite, ascorbic acid, bovine serum albumin (BSA), dexamethasone, proline, and TGF-β, preferably all of the above components.

In accordance with an embodiment of the present invention, a combination of 1% antibiotic-antimycotic, 1.0 mg/mL insulin, 0.55 mg/mL human transferrin, 0.5 mg/mL sodium selenite, 10 µg/ml TGF-β1, 50 µg/mL ascorbic acid, 1.25 mg/mL bovine serum albumin (BSA), 100 nM dexamethasone, 40 µg/mL proline, Dulbecco's Modified Egle Medium-High Glucose containing β; DMEM-HG.

The preparing method of the cartilage-regenerating composition includes (d) incubating the cell pellet in cartilage differentiation medium.

Since the cell pellet incubation under the cartilage differentiation medium changes the compressive strength, adherence and application property according to the incubating period, an incubating period can be set to provide a cartilage regeneration composition suitable for the affected part. The incubation can be preferably performed in a three-dimensional incubation, and the incubation period can be performed within 4 weeks, preferably 1 day to 21 days, more preferably 3 weeks.

The present invention also provides a pharmaceutical composition for treating a cartilage defect disease comprising, as an active ingredient, a cartilage regeneration composition comprising a fetal cartilage tissue-derived cell and an extracellular matrix derived from a fetal cartilage tissue.

The cartilage-regenerating composition including the fetal cartilage tissue-derived cell and the fetal cartilage tissue-derived extracellular matrix is as described above.

As described above, "cartilage defect disease" refers to a disease caused by cartilage defects, injuries, or defects caused by cartilage, cartilage tissue and/or joint tissues (synovial membrane, articular capsule, cartilaginous bone, etc.) injured by mechanical stimulation or inflammatory reaction. Such cartilage defect diseases include, but are not limited to, degenerative arthritis, rheumatoid arthritis, fractures, muscle tissue damage, plantar fasciitis, humerus ulcer, calcified myositis, or joint damage caused by fracture nonunion or trauma.

According to the present invention, the pharmaceutical composition for treatment may further include a pharmaceutically acceptable carrier in addition to the cartilage-regenerating composition contained as an active ingredient.

According to the present invention, the pharmaceutically acceptable carrier to be contained in the pharmaceutical composition, which is usually used in the preparing, includes, but is not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrups, methylcellulose, methylhydroxybenzoate, propyl hydroxybenzoate, talc, magnesium stearate, and mineral oil. According to the present invention, the pharmaceutical composition may additionally include a lubricant, a wetting agent, a sweetening agent, a flavoring agent, an emulsifying agent, a suspending agent, a preservative, etc. in addition to the above-mentioned components. Suitable pharmaceutically acceptable carriers and preparing thereof are described in detail in Remington's Pharmaceutical Sciences (19th ed., 1995).

According to the present invention, the pharmaceutical composition may be administered parenterally, and in the case of parenteral administration, it may be administered directly to cartilage defect, damage, or defect site.

According to the present invention, an appropriate amount of administration (preferably, transplantation) of the pharmaceutical composition may be variously prescribed by factors such as the preparing method, the mode of administration, and the age, weight, sex, pathological condition, and responsiveness of the patient. In the meantime, according to the present invention, the amount of administration (preferably the amount of transplantation) of the pharmaceutical composition may vary depending on the size and type of the affected part, but preferably 2 to 5 cartilage-regenerating compositions per $cm^3$ of the affected part, more preferably 3 or 4 cartilage-regenerating compositions may be administered (transplanted).

In the present invention, the pharmaceutical composition preferably provides the pharmaceutical composition including the cartilage-regenerating composition which can be injected directly into the affected part. According to an exemplary embodiment of the present invention, the cartilage-regenerating composition which can be injected directly into the affected part may be an injection formulation.

In the present invention, the pharmaceutical composition which can be directly injected into the affected part and includes the cartilage-regenerating composition as an effective ingredient may be formulated into a form capable of being directly injected into the affected part, and one of the preferable administration methods and preparing methods is an injection. The injection may be manufactured by using an aqueous solvent such as a physiological saline solution, a ring gel solution, a Hank solution or a sterilized aqueous solution, a vegetable oil such as an olive oil, a higher fatty acid ester such as ethyl oleic acid and a non-aqueous solution such as ethanol, benzyl alcohol, propylene glycol, polyethylene glycol or glycerin. For mucosal permeation, a non-penetrating agent known in the art suitable for the barrier to be passed may be used, and stabilizers for preventing deterioration may include ascorbic acid, sodium hydrogen sulfite, BHA, tocopherol, EDTA etc., and a pharmaceutically acceptable carrier such as an emulsifier, a buffer for controlling the pH, a preservative for inhibiting the growth of microorganisms such as phenylmercury nitrate, thimerosal, benzalkonium chloride, phenol, cresol, benzyl alcohol and the like may be further included.

The present invention also provides a method for treating a cartilage defect disease by administering (preferably transplantation) a pharmaceutically effective amount of a cartilage regeneration composition including a fetal cartilage tissue-derived cell and an extracellular matrix derived from a fetal cartilage tissue to a patient.

An object of the present invention is also to provide a cartilage-regenerating composition including cells of a fetal cartilage tissue-derived cell and a fetal cartilage tissue-derived extracellular matrix in the preparing of a medicament for treating the cartilage defect disease.

The matters mentioned in the use, composition and treatment method of the present invention are applied equally unless they are mutually contradictory.

Advantageous Effects

According to the present invention, the cartilage-regenerating composition may produce a three-dimensional tissue of a size suitable for use as a cartilage without a scaffold, may be easily transplantable regardless of the size and shape of the cartilage defect at the site of administration since it can be administered in the form of a gel, but has high application and adhesion, may exhibit a high binding ability to the host tissue, and may have a phenotype of mature cartilage tissue, thereby exhibiting an excellent cartilage regeneration effect.

MODE FOR INVENTION

Hereinafter, exemplary embodiments of the present invention will be described in more detail. These embodiments are only for illustrating the present invention, and thus the scope of the present invention is not construed as being limited by these embodiments.

<Exemplary Embodiment 1> Preparing of Cartilage-Regenerating Composition

Figure 1:
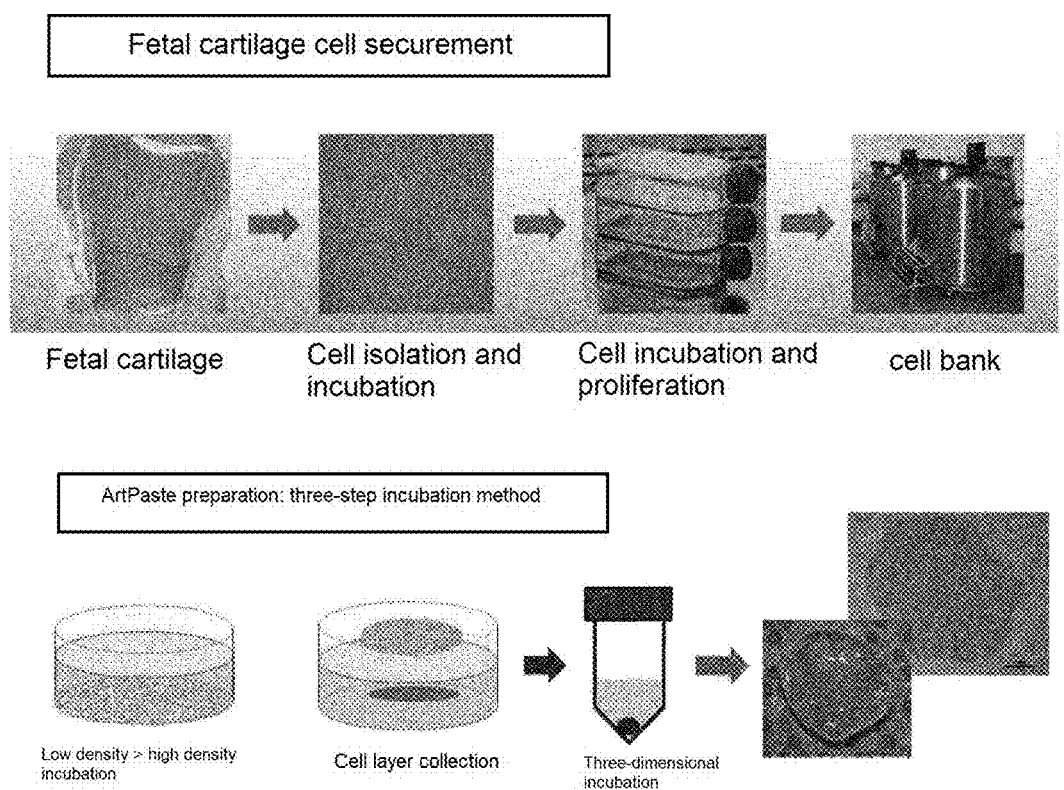
FIG. 1 illustrates a schematic view showing a preparing method of a cartilage-regenerating composition according to an exemplary embodiment of the present invention.

A schematic diagram of steps for producing a cartilage-regenerating composition is shown in FIG. 1, and the preparing method is as follows.

For the preparation of a cartilage-regenerating composition containing fetal cartilage tissue-derived cells and an extracellular matrix derived from fetal cartilage tissue, a fetus of 10 to 15 weeks (source: IRB NO. AJIRB-MED-SMP-10-268) from the knee joints.

Specifically, the cartilage tissues separated from the knee joints were washed with PBS (phosphated buffered saline), and then incubated with 0.2% (w/v) collagenase (Worthington Biochemical Corp., Lakewood, N.J.) in DMEM (Dulbecco's Modified Egle Medium, Gibco, Grand Island, N.Y.) for 4 hours. Chondrocytes released by completely digesting the cartilage tissues were centrifuged at 1700 rpm for 10 minutes, and then precipitated chondrocytes were resuspended in a tissue culture dish (density of 1×106 cells per 150 mm (dia.)×20 mm (h) per culture dish).

The chondrocytes were diluted in DMEM supplemented with 10% fetal bovine serum (FBS), 50 units/mL penicillin and 50 µg/mL streptomycin, and then incubated for 15-18 days in monolayers. After the incubation, the medium was removed, and 0.05% trypsin-EDTA (Gibco) was added to obtain a cell membrane bound to the extracellular matrix. When the cell membrane bound with the cells and the extracellular matrix was obtained, the cell membrane including the cells and the extracellular matrix were obtained at one time without pipetting the cells after 0.05% trypsin-EDTA (Gibco) treatment.

The obtained cell membrane bound with the cells and the extracellular matrix was placed in a tube of 50 ml including cartilage differentiation medium (1% antibiotic-antimycotic, 1.0 mg/mL insulin, 0.55 mg/mL human transferrin, 0.5 mg/mL sodium selenite, 50 µg/mL ascorbic acid, 1.25 mg/mL bovine serum albumin (BSA), 100 nM dexamethasone, 40 µg/mL proline) and 10 µg/ml TGF-β (Dulbecco's Modified Egle Medium-High Glucose; DMEM-HG) and centrifuged at 250×g for 20 minutes to prepare a pellet-shaped structure.

The prepared cell pellets were placed in an incubator dish containing the same cartilage differentiation medium as that of the above composition and incubated for one week, two weeks, and three weeks in an incubator with 5% carbon dioxide at 37° C. to prepare a cartilage-regenerating composition.

Figure 2:
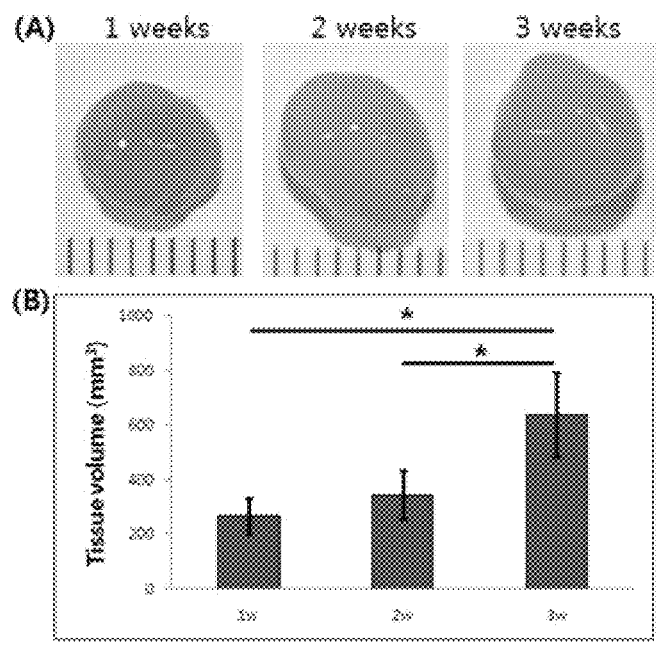
FIG. 2 illustrates a photograph showing the appearance of a gel-like cartilage-regenerating composition prepared by incubating for one week, two weeks, or three weeks, and a volume of the tissue according to an exemplary embodiment of the present invention.

The photographs and tissue volume of the cartilage-regenerating composition prepared by the above-described method are illustrated in FIG. 2. FIG. 2(A) illustrates the naked eye (1 mm per gradation) of the tissue, and FIG. 2(B) illustrates the volume of the tissue. As shown in FIG. 2, a spherical gel-type composition was prepared according to the preparation of the cartilage-regenerating composition, and it was seen that the size and volume of the gel-type composition increased with the incubation period. It was prepared from cell pellet by culturing cells and extracellular matrix in a spherical form, and it was seen that shape deformation was easily occurred since it corresponded to a gel type.

<Exemplary Embodiment 2> Histological Analysis of Cartilage-Regenerating Composition The cells were fixed in 4% formalin for 1 week in the course of preparing the composition for cartilage-regenerating from the cell pellet of the exemplary embodiment 1, and then embedded in paraffin and cut to a thickness of 4 µM. Then, for detection of accumulated sulfated proteoglycan, the cross-sections were subjected to Sarfanin-O staining and hematoxylin (H & E).

Figure 3:
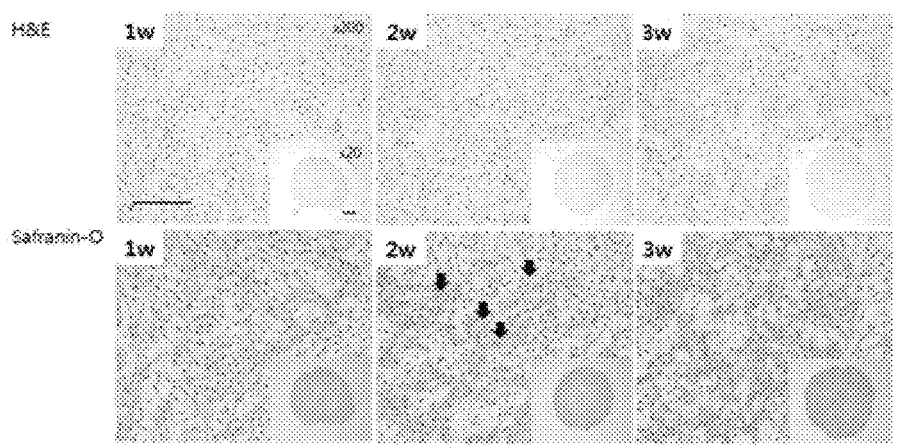
FIG. 3 illustrates results of a gel-type cartilage regeneration composition prepared by incubating for one week, two weeks, or three weeks and comparing the results with Safranin-O staining and hematoxylin & & Eosin) according to an exemplary embodiment of the present invention.

The result is illustrated in FIG. 3.

As checked in FIG. 3, it was seen that the cell interval became wider and the cell shape became similar to chondrocytes in hematoxylin (H & E) as the time elapsed from one week to three weeks. In addition, it was seen that Sarfanin-O staining, which is a method of staining protein sugar, increases an amount of protein sugar at two weeks and three weeks to form lacuna, which can be seen in cartilage.

<Exemplary Embodiment 3> Total Content of Glycosaminoglycan (GAG) and Analysis of Cartilage-Regenerating Composition The moisture content, DNA content, glycosaminoglycan content, and hydroxyproline content of the cartilage-regenerating composition, which were incubated for one week, two weeks, and three weeks, were measured.

To that end, the moisture content of the cartilage-regenerating composition was measured in weight after the incubation, and lyophilized to be expressed as a percentage when compared it with a dry weight thereof. For the DNA content, the amount of DNA contained in 1 mg of dry weight was measured using PicoGreen Kit. For the glycosaminoglycan content, it was decomposed for 16 hours in a 60° C. papain solution (5 mM L-cysteine, 100 mM Na2HPO4, 5 mM EDTA, papain type III 125 µg/mL, pH 7.5) and then centrifuged at 12,000×g for 10 minutes, and absorbance was measured at 550 nm wavelength using ELISA Reader (BIO-TEK, Instruments, INC., USA) by the centrifuged supernatant and DMB (dimethylmethylene-blue) colorimetric analysis (colorimetric assay, Heide, T. R. and Gernot, J., Histochem. Cell Biol., 112:271, 1999). For total collagen content, it was dissolved in an HCl solution, treated at 121° C. for 10 minutes, and centrifuged at 12,000×g for 10 minutes, and absorbance was measured at 480 nm wavelength using ELISA Reader by mixing the centrifuged supernatant, chloramine T, and dimethylamino-benzaldehyde. Normal cartilage was used as a control group.

Figure 4:
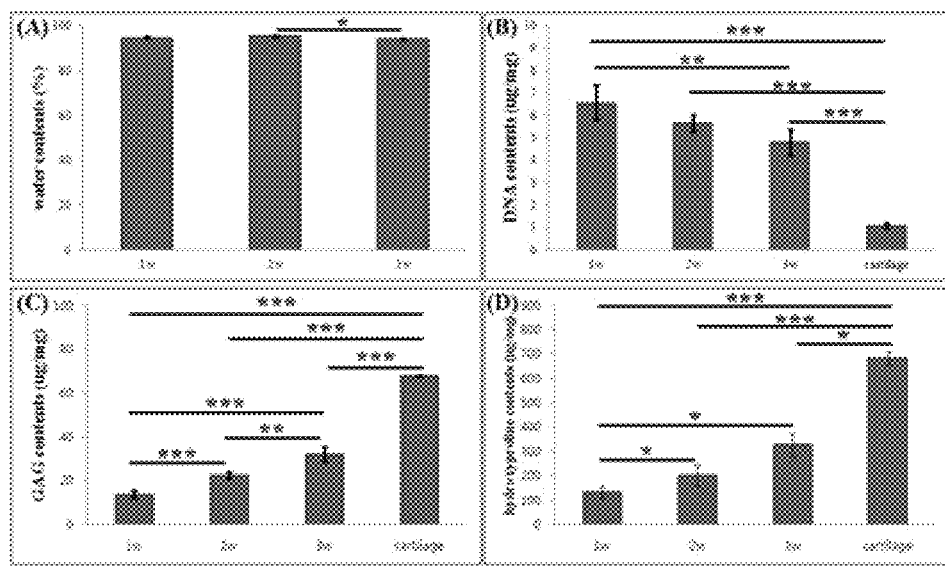
FIG. 4 illustrates moisture content, DNA content, glucosamine glycans, and hydroxyproline content of a cartilage-regenerating composition prepared according to an exemplary embodiment of the present invention by incubating for one week, two weeks, or three weeks.

The result is illustrated in FIG. 4.

As checked in FIG. 4, it was seen that the moisture content was 95% on average, the amount of DNA was 6.88±1.01 µg/mg for one week, 5.74±0.40 µg/mg per week, and 5.05±0.77 µg/mg for three week, and the DNA amount was reduced as the time elapsed, but there is no change in the DNA amount when compared with the increase in size. The biochemically analyzed total GAG contents were increased to 16.76±2.8 µg/mg (dry weight) for one week, 35.87±5.1 µg/mg (dry weight) for two weeks, and to 48.98±8.0 µg/mg as the incubation period is increased. In particular, it was seen that the total GAG content of the cartilage-regenerating composition has become closer to the natural cartilage tissue as the incubation period becomes longer, considering that the GAG content in the natural cartilage tissue is about 62.8±5.1 µg/mg (dry weight). The amount of hydroxyproline was increased to 7.78±1.89 µg/mg for one week, 40±11.74 µg/mg for two weeks, and 87.2±3.57 µg/mg at 3 weeks, respectively as the incubation period is increased.

<Exemplary Embodiment 4> Measuring Physical Strength of Cartilage-Regenerating Composition The compressive strength of the cartilage-regenerating composition was checked using a universal testing machine (Model H5K-T, HTE, UK).

The cartilage-regenerating composition prepared by performing the incubation for one week, two weeks, and three weeks in the exemplary embodiment 1 was first measured for compressive strength under an in vitro condition, and the cartilage-regenerating composition, which was incubated in vitro for two weeks, was incubated in ex vivo model for two weeks, four weeks, and eight weeks, and then the compressive strength was measured to compare the changes in compressive strength by in vivo incubation. The Ex vivo model was created as follows. First, cartilage tissue (Ajou University Hospital, IRB No. AJIRB-MED-SMP-11-205), which was discarded after knee arthroplasty for osteoarthritis patients, was collected to make defects similar in shape to actual cartilage damage, and then the cartilage-regenerating composition was inserted into the defect site and transplanted into the rat subcutaneously to be incubated for two, four, and eight weeks.

Each sample (n=6) was photographed, and then the cross-section and the height were calculated by using an image J program, in order to measure the compressive strength. Each sample was pressed at a rate of 1 mm/min until the strain of the tissue reached 20%, and then the value of Young's modulus was measured at a strain of 10 to 16%, and the in vitro and ex vivo results were illustrated in FIG. 5.

Figure 5:
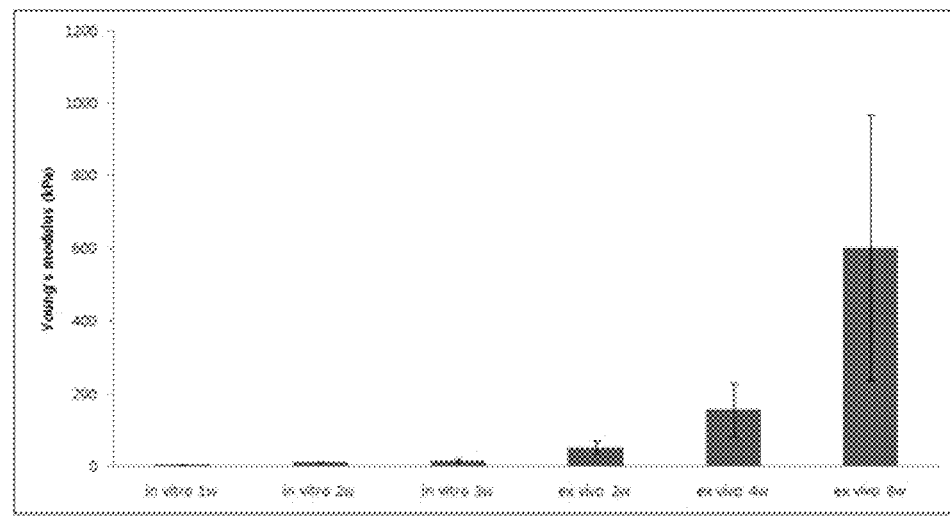
FIG. 5 illustrates results of confirming the young's modulus (kPa) of the cartilage-regenerating composition prepared according to an embodiment of the present invention and the cartilage-regenerating composition administered ex VIVO.

As checked in FIG. 5, the cartilage-regenerating composition showed 5.21 kPa for one week, 10.62 kPa for two weeks, and 15.83 kPa for three weeks in vitro, maintaining the gel shape. However, the intensity increased to 50.81 kPa for two weeks, 155.58 kPa for four weeks, and 602.04 kPa for eight weeks in the ex vivo state, and the intensity increased to a level similar to normal cartilage tissue over time in an in vivo environment.

It was seen that from the above results that the cartilage-regenerating composition according to the present invention was able to have a compressive strength similar to that of cartilage tissue when administered to human body.

<Exemplary Embodiment 5> Checking Whether or not a Cartilage-Regenerating Composition was Produced Depending on Cell Source Difference The availability of a cartilage-regenerating composition including a fetal cartilage tissue-derived cell and an extracellular matrix derived from a fetal cartilage tissue according to the present invention was checked by varying cell sources.

The cartilage-regenerating composition was prepared using the cell source as a human infant cartilage in the same manner as in the exemplary embodiment 1, in order to compare it with the cartilage-regenerating composition according to the exemplary embodiment 1.

The two cartilage-regenerating compositions were incubated in a cartilage medium for three weeks to be used. The cartilage-regenerating compositions were fixed in 4% formalin and then embedded in paraffin, cleaved to 4 μm thickness, to perform Sarfanin-O staining on the cross-section.

Figure 6:
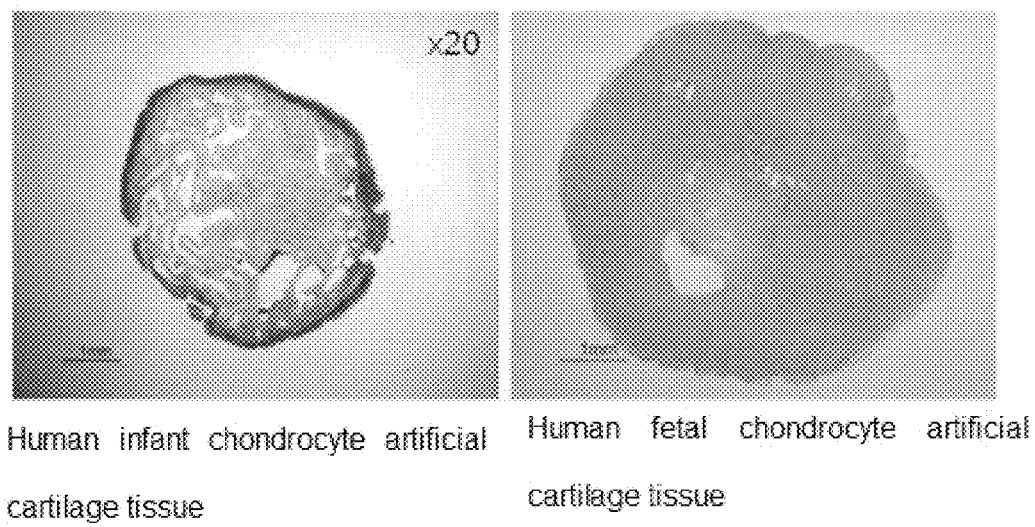
FIG. 6 illustrates checked results of a histological staining (Safranin O) performed for visualizing a cartilage-regenerating composition prepared according to an exemplary embodiment of the present invention and the amount of protein sugars in the cartilage-regenerating composition prepared with infant cartilage cells.

The result is illustrated in FIG. 6.

As checked in FIG. 6, it was seen that in the case of human infant chondrocyte artificial cartilage tissue, proteoglycan was expressed only outside the tissue, whereas in the case of human fetal chondrocyte artificial cartilage tissue, the protein sugar is distributed evenly throughout the tissue, resulting in confirming the excellent effect of the cartilage-regenerating composition according to the present invention. That is, it was seen that the cartilage-regenerating composition according to the present invention may be prepared by using fetal fatal chondrocyte and the extracellular matrix thereof as the cell sources.

<Exemplary Embodiment 6> Analysis of Coating Property of Cartilage-Regenerating Composition The coating property (spreadability) of the cartilage-regeneration composition prepared in the exemplary embodiment 1 was measured using a universal testing machine (Model H5K-T, HTE, UK).

An experimental method for measuring the coating property was set up considering the physically characteristic of the cartilage-regeneration composition. The cartilage-regeneration composition (n=6) was weighed and placed on a flat floor, and a force of 5 N for 1 second at a rate of 1 mm/min was applied vertically to the sample using a jig. After photographing the sample, the image was analyzed with an image J program to calculate the area of the sample spread on the floor.

Figure 7:
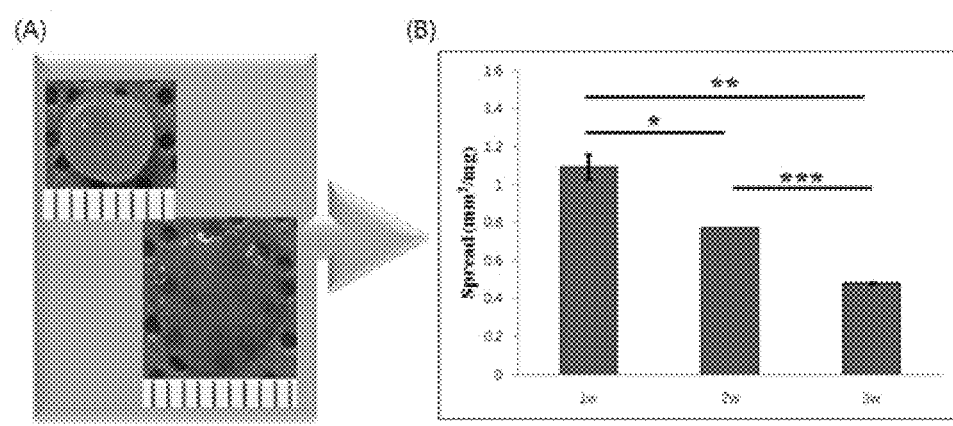
FIG. 7 shows results of checking the coating property (spreadability) of a gel-like cartilage-regenerating composition prepared by incubating for one week, two weeks, or three weeks according to an exemplary embodiment of the present invention.

The result is illustrated in FIG. 7.

FIG. 7(A) illustrates a result of checking the coating property, and FIG. 7(B) illustrates numerical values thereof. As checked in FIG. 7, it was seen that as a results of analyzing the coating property of the sample, the coating property showed 1.09±0.062 mm$^2$ for one week, 0.77±0.001 mm$^2$/mg for two weeks, and 0.48±0.004 mm$^2$/mg for three weeks, and the coating property per unit weight as the time elapsed. This seemed to be related to the result that the cartilage-regenerating composition is increased in strength and tissue becomes harder as the incubation period elapses in the exemplary embodiment 4.

Techniques of generally known cartilage-regenerating materials have been developed with emphasis only on the strength to withstand loads, and thus there has been a problem that a cartilage-regenerating material cannot be suitably applied on the cartilage damage site.

That is, it was seen that the cartilage-regenerating composition according to the present invention exhibits a characteristic of being spread and applied onto the damaged area when inserted into the cartilage damage site unlike the known cartilage regeneration materials.

<Exemplary Embodiment 7> Analysis of Adherence of Cartilage-Regenerating Composition The adherence of the cartilage-regeneration composition prepared in the exemplary embodiment 1 was measured using a universal testing machine (Model H5K-T, HTE, UK).

The cartilage tissue of the patient to be discarded after surgery was donated with consent. A cartilage damage model was prepared using a 6 mm biopsy punch on the surface of the cartilage tissue of the patient, and the prepared cartilage-regenerating composition was inserted. Then, a jig with a diameter of 5 mm was placed in contact with the inserted cartilage-regenerating composition and pulled at a rate of 1.3 mm/min to measure the resistance until the jig was separated from the cartilage-regenerating composition. Alginate, which is a gel-like biomaterial, was inserted into the cartilage damage model in the same manner to compare its adherence.

Figure 8:
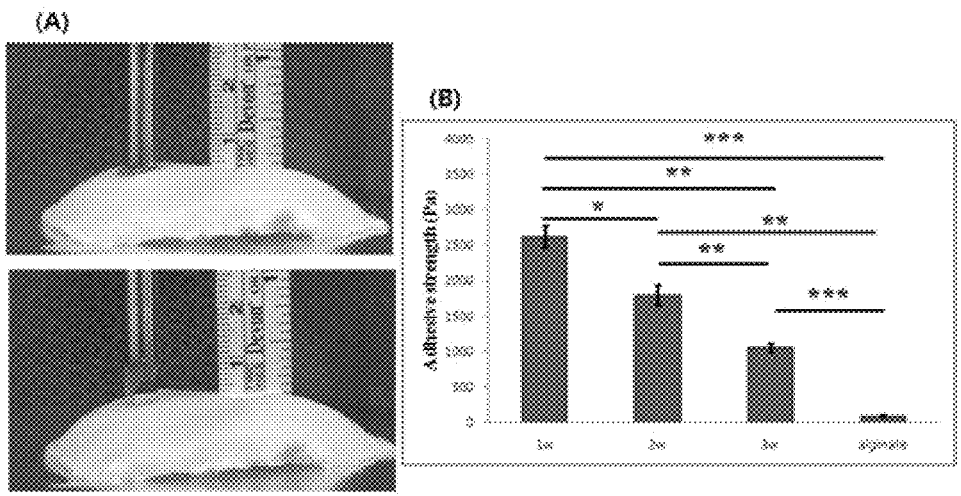
FIG. 8 shows results of checking the adherence of a gel-like cartilage-regenerating composition prepared by incubating for one week, two weeks, or three weeks according to an exemplary embodiment of the present invention.

The result is illustrated in FIG. 8.

FIG. 8(A) illustrates a photograph showing results of testing the adherence of the chondral defect by using an adult cartilage tissue in the above experimental model, and FIG. 8B illustrates results of checking the change in the adherence of the cartilage-regenerating composition according to an incubation period.

As checking in FIG. 8B, it was seen that as a results of analyzing the adherence of the sample depending on the incubation period, the adherence showed 2.624±0.154 kPa for one week, 1.799±0.146 kPa for two weeks, and 1.058±0.067 kPa for three weeks, and as the time elapsed, the cartilage-regenerating composition and the adhesion of patient cartilage tissue was slightly decreased, and the adhesion was significantly higher than that of the alginate (0.094 0.014 kPa) used as the control group.

From the above results, it was seen that the cartilage-regenerating composition according to the present invention has a very high adhesion in cartilage tissue compared to the conventional gel-type sample, and the adhesion may be adjusted to an appropriate level depending on the incubation period.

<Exemplary Embodiment 8> Checking Cartilage-Regenerating Composition Depending on Medium Composition The cartilage-regenerating composition were prepared in the same manner as in the method of the exemplary embodiment 1, while changing the medium composition in order to check generation change of the cartilage-regenerating composition depending on the change in the medium composition.

A composition prepared by the 3-week incubation using the cartilage-regenerating composition prepared in the exemplary embodiment 1 and the differentiation medium containing fetal bovine serum (Medium composition: 1% antibiotic-antimycotic, 1.0 mg/mL insulin, 0.55 mg/mL human transferrin, 0.5 mg/mL sodium selenite, Dulbecco's Modified Egle Medium-High Glucose (DMEM-HG) containing Ascorbic acid, 100 nM dexamethasone, Dulbecco's Modified Egle Medium-High Glucose containing 40 µg/mL proline and 10 ng/ml TGF-β; DMEM-HG) as a medium was analyzed through Sarfanin-O staining.

Each of the above compositions were fixed in 4% formalin and then embedded in paraffin, cleaved to 4 µm thickness, to perform Sarfanin-O staining on the cross-section.

Figure 9:
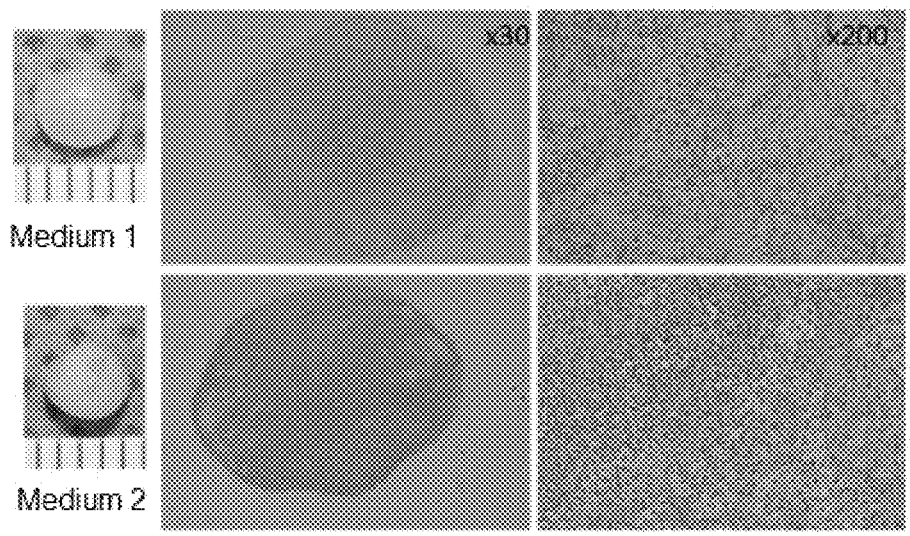
FIG. 9 illustrates results of checking a formation degree of a cartilage-regenerating composition depending on a medium composition.

The result is illustrated in FIG. 9.

As checked in FIG. 9, it was seen that the cartilage-regeneration composition prepared in the cartilage differentiation medium (medium 1) showed GAG throughout the general cells, but in the composition prepared in the differentiation medium containing the fetal bovine serum (medium 2), cartilage GAG remained and the cells in the center were killed.

It was seen from the result that the cartilage medium corresponded to a suitable medium composition in the preparation of the cartilage-regeneration composition according to the present invention.

<Exemplary Embodiment 9> Checking Histological and Immunological Characteristics of Cartilage-Regenerating Composition The cartilage-regenerating composition prepared for two weeks in the cartilage medium according to the exemplary embodiment 1 was transplanted into a block of a same shape as a cartilage damage model, and then incubated in the nude mouse hypodermically for two, four, eight, twelve weeks (w), and osteochondral autologous transplantation (OAT) which is generally used in clinical practice was used as a control group. The tissues were taken out, each block was fixed with 4% formalin, embedded in paraffin and cleaved to a thickness of 4 µm, and imunohistochemical staining was performed on the cross-section for visual confirmation of Safranin-O staining and amount of collagen. Immunostaining checked first collagen and second collagen.

Figure 10:
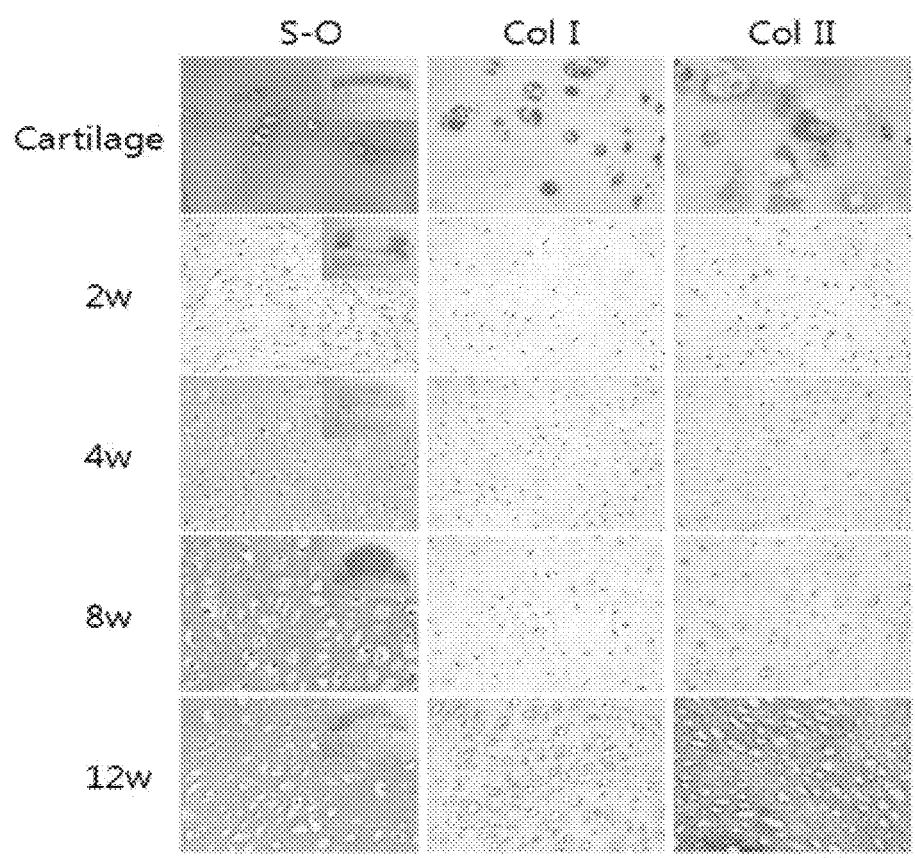
FIG. 10 illustrates results of incubating a cartilage-regenerating composition prepared according to an exemplary embodiment of the present invention, transplanting it in a human cartilage block, incubating it in a nude mouse subcutaneously, and then performing histological staining and immunostaining.

The result is illustrated in FIG. 10.

As checked in FIG. 10, it was seen that a shape similar to that of normal cartilage was observed over time after the cartilage-regenerating composition was transplanted. Specifically, safranin-O, which may detect the amount of protein sugars, showed little expression after two weeks of transplantation, but it was seen to be similar to normal cartilage over time. When the cartilage is demineralized, the amount of first collagen increases, but when it is differentiated into cartilage and differentiated into normal cartilage, the amount of second collagen increases. In ex vivo, the first and second collagens were not stained at two weeks, but the amount of second collagen increased with the passage of four weeks and eight weeks. After 12 weeks, the amount of collagen was similar to that of normal cartilage. Particularly, the expression of type II collagen, which is the most collagen in cartilage, reached to the level of normal cartilage at 12 weeks.

<Exemplary Embodiment 10> Checking In Vivo Attachment of Cartilage-Regenerating Composition Labeled with Fluorescence Expression Factor PKH-26

A cartilage-regenerating composition was prepared by incubating a cell labeled with the fluorescence expression factor PKH-26 on a cell surface thereof under the cartilage medium according to the method of the exemplary embodiment 1 to check whether the fluorescent expression factor PKH-26 was expressed on days 1 and 7 after the incubation.

Figure 11:
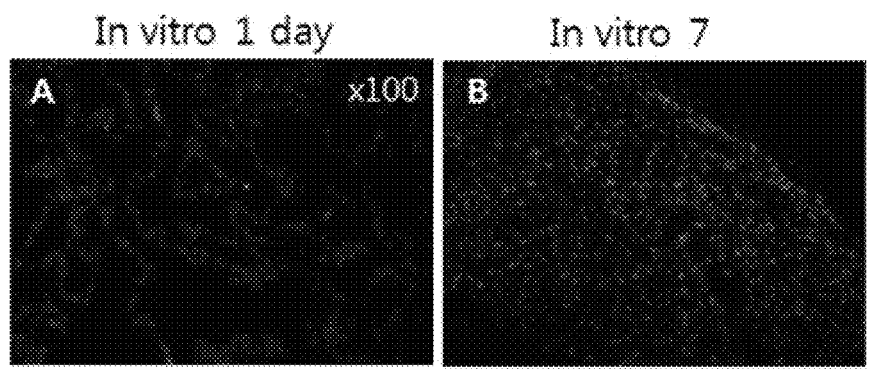
FIG. 11 illustrates results of checking the fluorescence expression of a cartilage-regenerating composition according to an exemplary embodiment of the present invention, labeled with a fluorescent expression factor PKH-26.

The result is illustrated in FIG. 11. As illustrated FIG. 11, it was seen that the expression of the fluorescent element was well performed in the cartilage-regenerating composition in vitro.

The prepared cartilage-regenerating composition was then transplanted into a partial cartilage damage model of the rat.

Specifically, an 8-week-old rat knee was incised, the cartilage of the femur was scratched with a curette of No. 12, and a cartilage regeneration composition with the fluorescent expression factor PKH-26 was transplanted.

On 3 and 7 days after the transplantation, the knees of the transplanted area were separated and slices were prepared with a 4 µm thickness using a freezing machine. The tissue and fluorescence expression of the injured area of the partial cartilage were checked using an optical microscope and a fluorescence microscope to examine whether the transplanted cartilage-regenerating composition remained. The result is illustrated in FIG. 12.

Figure 12:
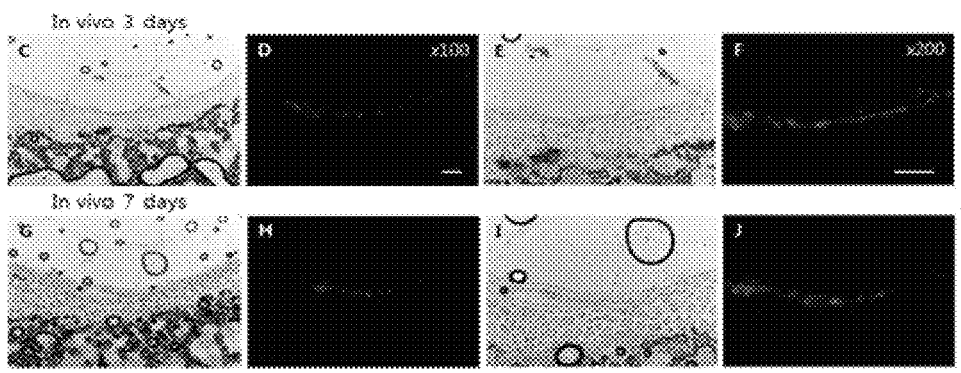
FIG. 12 illustrates results of checking the attachment of a cartilage damage site by transplanting a cartilage-regenerating composition prepared according to an exemplary embodiment of the present invention, labeled with a fluorescent expression factor PKH-26 to the damaged cartilage site.

As checked in FIG. 12, it was seen that the cartilage-regenerating composition adhered to the cartilage damage site on both 3 days and 7 days after the cartilage-regenerating composition was coated.

It was seen from the above result that the cartilage-regenerating composition was able to be coated and adhered to the affected part in vivo.

<Exemplary Embodiment 11> Checking Cartilage-Regenerating Effect Depending on Transplantation of Cartilage-Regenerating Composition in Partial Cartilage Damage Model of Rabbit The cartilage-regenerating composition incubated in a cartilage medium in vitro according to the exemplary embodiment 1 of the present invention is transplanted into a partial layer cartilage defect model of a rabbit produced in the exemplary embodiment 9.

At 6 and 12 weeks after transplantation, the regeneration of cartilage tissue was visually checked and the recovery of damage was checked by the histological staining, i.e., the saranin-O staining method.

Figure 13:
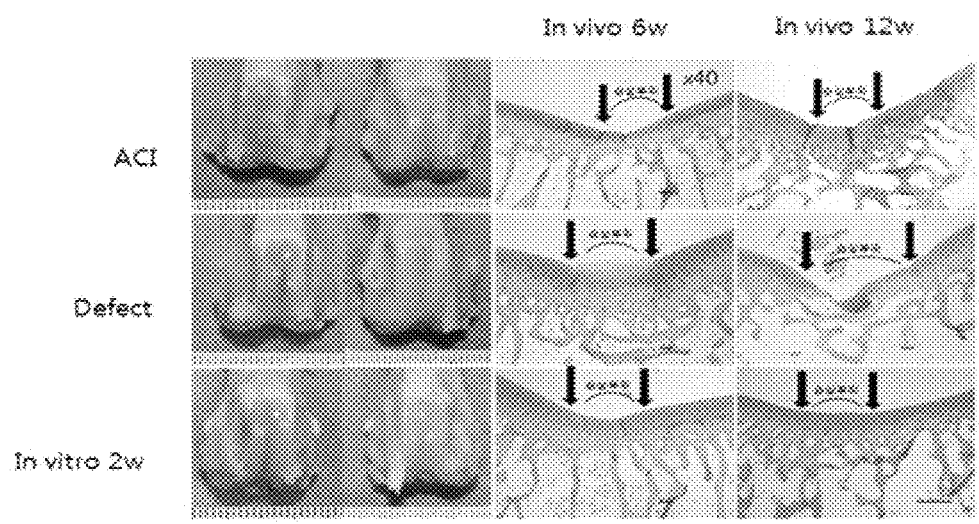
FIG. 13 illustrates results of checking regeneration of cartilage damage after transplanting a cartilage-regenerating composition for according to an exemplary embodiment of the present invention into a rabbit knee cartilage damage model through histological analysis.

The result is illustrated in FIG. 13.

In FIG. 13, ACI indicates an autologous chondrocyte implantation group, Defect indicates an untreated group, and in vitro 2w indicates a result of an experiment using the cartilage-regenerating composition incubated in the cartilage differentiation medium for two weeks.

As checked in FIG. 13, it was seen that when six and twelve weeks elapsed after the transplantation of the cartilage-regenerating composition according to the present invention, the normal tissue was restored to such an extent that the cartilage damage site was hardly observed, to be similar to be the normal tissue, and this effect was confirmed to be almost the same level as that of the autologous chondrocyte implantation group, which is a positive control group.

<Exemplary Embodiment 12> Checking Cartilage-Regenerating Effect Depending on Transplantation of Cartilage-Regenerating Composition in Knee Cartilage Damage Model of Monkey The cartilage damage model was constructed using a 3 mm biopsy punch at a femur medial condyle portion of the monkey knee. The cartilage-regeneration compositing was incubated in the damaged cartilage defect site for 2 weeks in vitro, and the cartilage regeneration degree was checked by imaging MRI for 8 weeks, 16 weeks, and 24 weeks. An untreated group was used as the control group.

The cartilage regeneration effect in the animal model was checked by MRI, safranin-O staining and hematoxylin & eosin staining.

Figure 14:
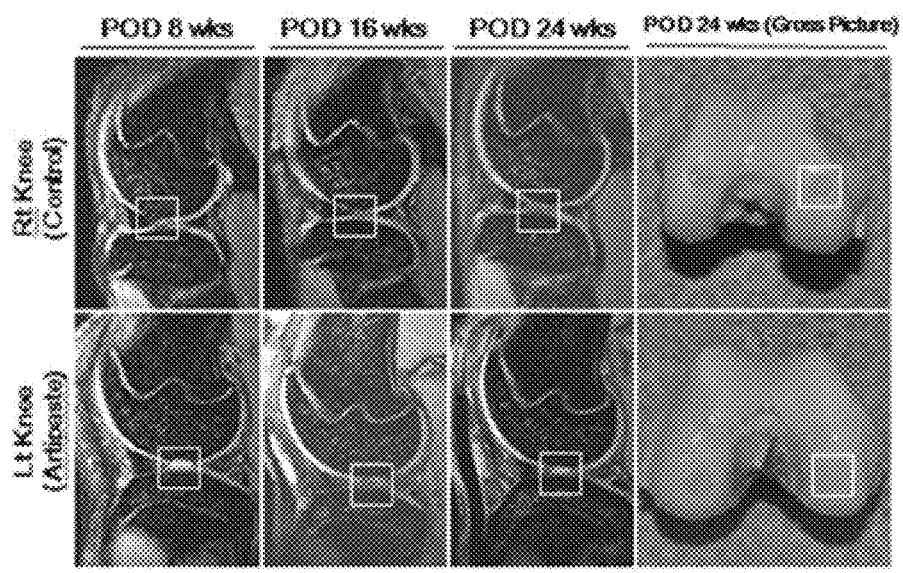
FIG. 14 illustrates results of checking regeneration of cartilage damage after transplanting a cartilage-regenerating composition for according to an exemplary embodiment of the present invention into a monkey knee cartilage damage model through MRI.
Figure 15:
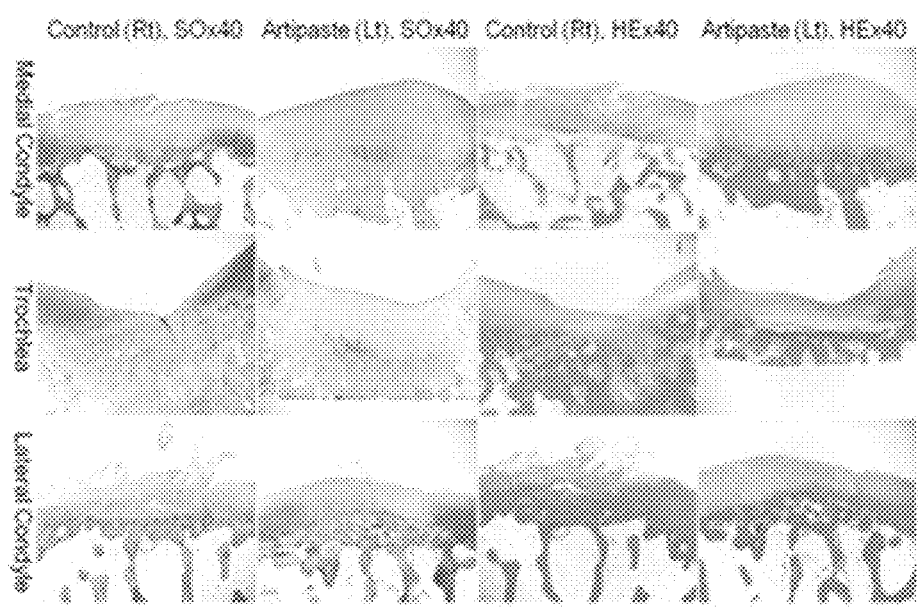
FIG. 15 illustrates results of checking regeneration of cartilage damage after transplanting a cartilage-regenerating composition for according to an exemplary embodiment of the present invention into a monkey knee cartilage damage model through tissue-dry.

FIG. 14 illustrates a result of an experiment analyzed through MRI. As checked in FIG. 14, it was seen that cartilage was formed in the group transplanted with the cartilage-regenerating composition over time in the MRI result for 24 weeks, and it was regenerated to normal cartilage such that a transplanted region was invisible when the animal was sacrificed after 24 weeks In addition, in FIG. 15, it was seen through results of safranin-O staining and Hematoxylin & Eosin staining that the cartilage collapsed and the amount of protein sugars was reduced in the control group where no treatment was performed, but the cartilage damage site was normally recovered in the experiment group to which the cartilage-regenerating composition was transplanted. In addition, it was seen that, in the case of the control group, the cartilage collapsed by damage even in the trochlea portion and the lateral condyle portion as well as the femur portion, i.e., the transplanted site, while the cartilage was formed in the transplanted site and the surrounding tissues were not affected in the group to which the cartilage-regenerating composition was transplanted.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

The invention claimed is:

1. A method of preparing a cartilage regenerating composition comprising a fetal cartilage tissue-derived cell and extracellular matrix derived from the fetal cartilage tissue-derived cell, the method comprising:
    (a) incubating a fetal cartilage tissue-derived cell in a 2-dimensional (2D) culture using a culture medium containing 10% serum to form a cell sheet;
    (b) obtaining a cell sheet including the cultured fetal cartilage tissue-derived cell and extracellular matrix expressed from the cultured fetal cartilage tissue-derived cell;
    (c) centrifuging the obtained cell sheet to obtain a 3-dimensional (3D) construct; and
    (d) incubating the 3D construct in a serum free-cartilage differentiation medium.

2. The cartilage-regenerating composition prepared by the method of claim 1,
    wherein the composition is gel-like and has the following properties in vitro:
    compressive strength at Young's modulus of less than 20 kPa when pressed at 1 mm/min speed;
    spreadability having a coverage of 0.1 to 2.0 $mm^2/mg$ when a force of 5 N was applied to a sample for 1 second at a speed of 1 mm/min; and
    adhesiveness of 0.5 to 5.0 kPa when a material was in contact with a jig having a diameter of 5 mm and an affected part to be attached thereto, to be pulled at a rate of 1.3 mm/min to be separated therefrom.

3. The cartilage-regenerating composition prepared by the method of claim 2, wherein the cartilage-regenerating composition has the following properties:
    compressive strength at Young's modulus of less than 0.2 to 20 kPa when pressed at 1 mm/min speed;
    spreadability having a coverage of 0.2 to 1.7 $mm^2/mg$ when a force of 5 N was applied to a sample for 1 second at a speed of 1 mm/min; and
    adhesiveness of 0.9 to 4.5 kPa when a material was in contact with a jig having a diameter of 5 mm and an affected part to be attached thereto, to be pulled at a rate of 1.3 mm/min to be separated therefrom.

4. The cartilage-regenerating composition of claim 2, wherein the cartilage-regenerating composition exhibits a characteristic of mature cartilage by enhancing expression of glycoprotein and collagen under an in-vivo condition.

5. A pharmaceutical composition for treating a cartilage defect disease comprising the cartilage-regenerating composition according to claim 2 as an active ingredient.

6. The pharmaceutical composition of claim 5, wherein the cartilage defect diseases include at least one of degenerative arthritis, rheumatoid arthritis, fractures, muscle tissue damage, plantar fasciitis, humerus ulcer, calcified myositis, and joint damage caused by fracture nonunion and trauma.

7. A method for treating a cartilage defect disease by administering to a patient a pharmaceutically effective amount of the cartilage regenerating composition according to claim 2.

* * * * *